(12) United States Patent
Simionescu et al.

(10) Patent No.: US 9,005,289 B1
(45) Date of Patent: Apr. 14, 2015

(54) TISSUE ENGINEERED NUCLEUS PULPOSUS REPLACEMENT

(75) Inventors: Dan Simionescu, Pendleton, SC (US); Jeremy Mercuri, Easley, SC (US)

(73) Assignee: Clemson University, Clemson, SC (US)

( * ) Notice: Subject to any disclaimer, the term of this patent is extended or adjusted under 35 U.S.C. 154(b) by 111 days.

(21) Appl. No.: 13/530,624

(22) Filed: Jun. 22, 2012

Related U.S. Application Data

(60) Provisional application No. 61/503,832, filed on Jul. 1, 2011.

(51) Int. Cl.
*A61F 2/44* (2006.01)

(52) U.S. Cl.
CPC .. *A61F 2/441* (2013.01); *A61F 2/44* (2013.01)

(58) Field of Classification Search
USPC ................ 606/93, 94, 105; 623/17.11, 17.12
See application file for complete search history.

(56) References Cited

U.S. PATENT DOCUMENTS

| | | | |
|---|---|---|---|
| 7,157,428 B2 | 1/2007 | Kusanagi et al. | |
| 7,195,912 B2 | 3/2007 | Takezawa et al. | |
| 7,217,294 B2 | 5/2007 | Kusanagi et al. | |
| 2004/0059418 A1 | 3/2004 | McKay et al. | |
| 2007/0149994 A1* | 6/2007 | Sosnowski et al. | 606/192 |
| 2007/0233259 A1 | 10/2007 | Muhanna et al. | |
| 2008/0021563 A1 | 1/2008 | Chudzik | |

OTHER PUBLICATIONS

Tedder, et al., "Stabilized collagen scaffolds for heart valve tissue engineering", Tissue Engineering: Part A, 2009, 15(6), 1257-1268.
Bron et al., "Repair, regenerative and supportive therapies of the annulus fibrosus: achievenents and challenges", Eur Spine J 2009; 18(3), 301-13.
Adams et al., The Biomechanics of Back Pain: Elsevier Lts; 2006.
Wilke et al., "New in vivo measurements of pressures in the intervertebral disc in daily life", Spine 1999, 24(8), 755-62.
Mow et al., Basic Orthopedic Biomechanics. Philadelphia: Lippincott-Raven, 1997.

* cited by examiner

*Primary Examiner* — Andrew Yang
(74) *Attorney, Agent, or Firm* — Dority & Manning, P.A.

(57) ABSTRACT

A nucleus pulposus replacement is described that includes a containment balloon that can sequester synthetic and/or tissue engineered fill material(s) in the nucleus pulposus region of the IVD thus mitigating migration and expulsion of the fill materials. The containment balloon can be formed of a biocompatible material that includes the structural proteins elastin and collagen. The containment balloon is joined to a closure device that can be used to deliver a fill material, e.g., a hydrogel, to the interior of the containment balloon following implantation of the replacement device in the intervertebral disc area.

32 Claims, 7 Drawing Sheets

TISSUE ENGINEERED NUCLEUS PULPOSUS REPLACEMENT

CROSS REFERENCE TO RELATED APPLICATIONS

This application claims filing benefit of U.S. Provisional Patent Application Ser. No. 61/503,832 having a filing date of Jul. 1, 2011, which is incorporated herein in its entirety by reference.

BACKGROUND

Intervertebral disc (IVD) degeneration is marked by detrimental changes that occur within the IVD structure. IVD degenerative changes appear to initiate within the central region of the IVD known as the nucleus pulposus. Accordingly, many early-stage interventional therapies are being investigated targeting the mitigation or reversal of the degenerative process during its existence in the nucleus pulposus.

Conservative estimates from 2006 indicate that nearly 640,000 individuals were admitted to U.S. hospitals for IVD-associated maladies accounting for $7.6 billion in direct costs. These staggering statistics provide the impetus for research into development of new treatment strategies including surgical techniques and tissue engineering approaches to regenerating the IVD.

Current treatment options include non-surgical management as an initial approach. Unfortunately, non-surgical treatment is only effective in about two-thirds of patients. Failure of such conservative treatment warrants more invasive surgical interventions that can include the removal of a problematic IVD and its replacement with a metallic/polymeric artificial disc. Alternatively, the problematic IVD can be rendered immobile using metal hardware (e.g., rods and screws) thus reducing pain and instability. These surgical procedures are merely palliative and have major consequences associated with their utilization. Moreover, these are typically last resort options for the patient leaving a large gap in treatment options between ineffective non-surgical approaches and current last resort surgical options. To bridge this gap, nucleus pulposus replacement has shown promising advancements as an early-stage treatment to fight IVD degeneration.

Two approaches have been followed thus far in developing nucleus pulposus replacement technology. The first of these is a purely material science approach based upon utilization of synthetic polymers to construct pre-formed or in situ-cured injectable polymeric materials that can replace and mimic the biomechanics of the native nucleus pulposus. The second approach to developing a nucleus pulposus replacement is based upon the principles of tissue engineering and utilizes a combination of cells, scaffolds and various chemical and/or mechanical cues to regenerate a healthy replacement tissue. Limitations to both approaches are becoming increasingly evident; the most prevalent of which is that of device migration and expulsion of synthetic materials due to the fact that they are inanimate and do not integrate intimately with surrounding host tissue.

What is needed in the art is a nucleus pulposus replacement and method of utilizing the nucleus pulposus replacement that addresses such short-comings.

SUMMARY

According to one embodiment, disclosed is a nucleus pulposus replacement. The nucleus pulposus replacement can include a containment balloon and a closure device. More specifically, the containment balloon can include a sheet that includes elastin and collagen. The closure device is joined to the containment balloon, and includes a one-way port for furnishing a fill material to an interior of the containment balloon.

A method of forming the nucleus pulposus replacement is also disclosed. For instance, the method can include joining the containment balloon to the closure device.

Also disclosed is a method for replacement of nucleus pulposus tissue. A method can include removal of nucleus pulposus tissue from an intervertebral disc followed by insertion of a nucleus pulposus replacement into the void formed by removal of the tissue. Following insertion, a fill material can be furnished via the one-way port to the interior of the containment balloon of the replacement.

BRIEF DESCRIPTION OF THE DRAWINGS

A full and enabling disclosure, including the best mode thereof, to one of ordinary skill in the art, is set forth more particularly in the remainder of the specification, including reference to the accompanying Figures, in which.

DETAILED DESCRIPTION

Reference will now be made in detail to various embodiments of the presently disclosed subject matter, one or more examples of which are set forth below. Each embodiment is provided by way of explanation, not limitation, of the subject matter. In fact, it will be apparent to those skilled in the art that various modifications and variations may be made to the present disclosure without departing from the scope or spirit of the disclosure. For instance, features illustrated or described as part of one embodiment, may be used in another embodiment to yield a still further embodiment. Thus, it is intended that the present disclosure cover such modifications and variations as come within the scope of the appended claims and their equivalents.

In general, the present disclosure is directed to a nucleus pulposus replacement. More specifically, the nucleus pulposus replacement includes a containment balloon that can sequester synthetic and/or tissue engineered fill material(s) in the nucleus pulposus region of the IVD thus mitigating migration and expulsion of the fill materials. The containment balloon can be formed of a biocompatible material that includes the structural proteins elastin and collagen. Beneficially, the containment balloon can include no or essentially no agents that can lead to immunogenic reaction and thus can be highly biocompatible with little likelihood of instigating a rejection reaction following implantation. In addition, the containment balloon can be surface modified so as to stabilize the balloon at the implantation site and/or to control degradation following implantation. For instance, surface modifications can be carried out such that integration of the balloon material with surrounding host tissue can be increased.

Figure 1:
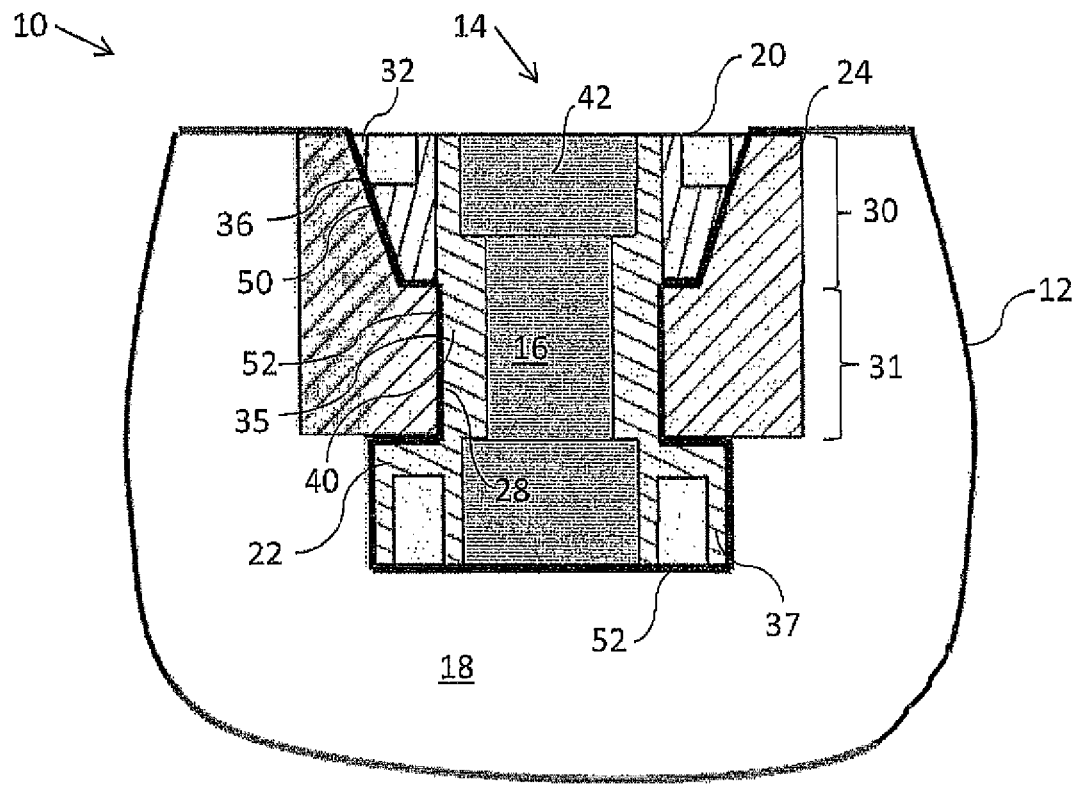
FIG. 1 illustrates one embodiment of a nucleus pulposus replacement as disclosed herein.

Referring to FIG. 1, one embodiment of a nucleus pulposus replacement 10 is illustrated. The nucleus pulposus replacement 10 includes a containment balloon 12 that can be filled with a fill material 18. The replacement 10 also includes a closure device 14. The closure device 14 includes a one-way port 16 that can be used to inject fill material 18 into the containment balloon 12 while preventing loss of the fill material 18 through the closure device 14 following fill. Taken together, the containment balloon 12 and the closure device 14 can form a nucleus pulposus replacement 10 that has utility in preventing the migration and expulsion of fill material 18 as may be utilized as nucleus pulposus replacement materials (both synthetic and tissue engineered). This is particularly important given the increase in the development of injectable in situ curing materials to date that exhibit potential as nucleus pulposus replacement material and may be incorporated in the device 10 as fill material 18.

The containment balloon 12 can be formed of a single or multiple layered sheets that include a high proportion of the structural proteins elastin and collagen. While the sheet can include synthetic elastin and/or collagen proteins, In general, the sheet(s) used to form the containment balloon 12 can be developed from any autogenic, allogenic, or xenogenic source tissue that includes elastin and collagen. By way of example, a sheet can be developed from vascular tissue (e.g., aortic tissue, vena cava tissue), tendons, ligaments, dermal tissue, pericardial tissue, dura mater, umbilical tissue, fascia, submucosal tissue, etc.

Collagen and elastin are the fibrous components of connective tissue and provide structural support, strength, and elasticity to sheet(s) of the containment balloon 12. Elastin is the protein constituent of connective tissue responsible for the elasticity and recoil of the tissue, while collagen provides both strength and structural characteristics to tissues. The relative proportion of collagen and elastin in connective tissue will vary depending upon the function of the tissue. For instance, elastin is the most abundant extracellular matrix protein found in the aortic wall, while collagen is the primary extracellular matrix protein in stronger, less flexible tissues such as cartilage, tendons, and ligaments. Beneficially for the presently disclosed nucleus pulposus replacement materials, the collagen and elastin of tissue function as fibrous reinforcement throughout the tissue, and a tissue source for formation of the containment balloon can be chosen that can exhibit strength, flexibility, and high biocompatibility.

To increase the biocompatibility of the sheet(s) used to form the containment balloon, the source tissue can be treated to remove immunogenic materials. For instance, the source tissue can be treated according to any known method to decellularize the source material. One exemplary method for decellularization of connective tissue has been previously described by Tedder, et al. (Tissue Engineering: Part A, 2009, 15(6), 1257-1268). Briefly, the treatment process can include cell lysis by hypotonic shock, and treatment with a detergent decellularization solution that can include, e.g., sodium-deoxycholate, Triton® X-100, ethylenediaminetetracetic acid, sodium azide, etc., or combinations thereof. Following, the source tissue can be treated with nucleases to fully digest nucleic acids of the source tissue.

Through pretreatment of the source tissue so as to remove immunogenic factors from the tissue, a highly biocompatible sheet can be formed that can support human cell viability, proliferation and growth. This can not only reduce or eliminate rejection potential of the nucleus pulposus replacement following implantation, but can improve long-term integration of the replacement with surrounding tissue and increase the likelihood of long-term repair of the degenerated IVD, rather than merely palliative care as is currently the most common treatment option.

An individual collagen and elastin-containing sheet used to form the containment balloon will generally be isotropic in strength characteristics due to alignment of the fibrous proteins of the source tissue. Accordingly, to further enhance strength of the containment balloon, a plurality of individual sheets can be layered together with the fibrous ply of each individual sheet at an angle to that of adjacent sheet(s) to form a multi-laminar ply-angle-ply containment balloon material. For instance, multiple sheets can be assembled into a ply-angle-ply orientation to match (or nearly match) the characteristics of the native architecture of the surrounding annulus fibrosus following implantation.

A plurality of sheets can be aligned with one another and utilized as such, i.e., with no additional adherence materials between adjacent sheets. Alternatively, a tissue adhesive as is known in the art may be included between adjacent sheets to further increase adherence between the sheets. For example, a glutaraldehyde/albumin composite-based adhesive, a fibrin-based adhesive, a fibronectin-based adhesive, and the like may be utilized. In general, however, adhesive materials will not be necessary and adjacent sheets will adequately adhere to one another without the need for additional materials there between.

The angle between the ply of adjacent sheets can vary as desired so as to provide the desired strength characteristics to the multi-laminar material. For instance, when forming a two-sheet material, the sheets can be aligned with a 90° angle between the plies. Alternative alignments can be utilized as will be evident to one of skill in the art.

Other characteristics of the individual sheets and/or a multi-laminar material may also be adjusted as desired so as to provide desired characteristics to the containment balloon. For instance, the thickness of a single sheet can vary depending upon the source tissue utilized to form the sheet, the processing conditions used, etc.

In one embodiment, a single sheet can have an average thickness of between about 20 micrometers ($\mu$m) and about 100 $\mu$m, for instance between about 30 $\mu$m and about 80 $\mu$m, or between about 50 $\mu$m and about 70 $\mu$m.

The containment balloon can generally be porous and allow for the influx and efflux of biomolecules such as lower molecular weight molecules including but not limited to water, glucose, cytokines, and growth factors. Moreover, and depending upon the porosity of the containment balloon, the balloon can allow for the movement of cells, e.g., either influx of host cells and/or efflux of cells implanted in conjunction with the nucleus pulposus replacement across the containment balloon, which could aid in integration of the device with surrounding tissue as well as regeneration of nucleus pulposus tissue. For instance, in one embodiment a sheet that may be utilized in forming the containment balloon can have an average pour size of between about 8 $\mu$m and about 35 $\mu$m. However, porosity of the individual sheets and the formed containment balloon can vary, and formation processes can be varied so as to control porosity of the device. For instance, porosity of the containment balloon can be controlled by selection of the number and alignment of individual sheets used to form the containment balloon. By way of example, a higher number of sheets with a large variation in ply alignments can be used to decrease the overall porosity of the containment balloon.

The fibrous components of the containment balloon material can be cross-linked with collagen and/or elastin cross-linking agents. Cross-linking can be utilized to affect multiple characteristics of the device. For example, the level of cross-linking can influence the porosity of the containment balloon and the strength of the containment balloon. Any suitable cross-linking agent can be utilized. For example, collagen fixatives such a glutaraldehyde, carbodiimide, polyepoxides, etc. and/or elastin fixatives including polyphenolic compounds (tannic acid, pentagalloyl glucose, etc.) and the like can be utilized to cross-link the structural proteins of the containment balloon.

The containment balloon can exhibit excellent strength characteristics. Specifically, the burst strength of a containment balloon can resist stresses that exceed typical intradiscal pressures. For example, a containment balloon formed of a single sheet of decellularized material can have a burst strength of about 0.3 megapascal (MPa) or greater. A multi-laminar containment balloon can exhibit even higher burst strength. For instance, a containment balloon formed of a 2-ply sheet can have a burst strength of greater than about 0.7 mPa, or greater than about 0.8 mPa. In one embodiment, a containment balloon can exhibit a compressive stress before failure of greater than about 1 MPa, greater than about 1.2 MPa, or greater than about 1.3 MPa. Burst strength can be determined according to known practice, for instance according to a multi-axial burst test using a 10 kilonewton (kN) load cell operating at a speed of 25 mm/min.

Cross-linking of the containment balloon material can also be utilized to control the degradation characteristics of the material following implantation. For instance, a highly cross-linked material can degrade more slowly, while a lightly cross-linked material can degrade more quickly. Control of degradation rate can enhance or delay integration of the containment balloon material with host tissue that surrounds the balloon as well as with nucleus pulposus replacement material that can be provided as fill material inside the balloon.

The outer surface of the containment balloon can be modified, for instance to enhance adhesion to and/or integration with the surrounding material, which can also decrease the likelihood of migration of the device following implantation. For instance, the outer surface of the containment balloon can be augmented with one or more tissue adhesives as mentioned previously to enhance adhesion to the inner surface of the annulus fibrosus following implantation.

The porosity of the sheets used to form the containment balloon can also provide an excellent platform for utilizing the containment balloon as a drug delivery device. For example, the containment balloon can be pre-loaded (e.g., through simple perfusion techniques such as solution soaking) with one or more biologically active agents. By way of example, the containment balloon material can be loaded with one or more biologically active agents that can ameliorate IVD degeneration, analgesics, anti-apoptotic agents, antibiotics, anti-inflammatory agents, etc. Biologically active compounds as may be incorporated in or on the surface of the containment balloon can include, without limitation, tissue inhibitors of matrix metalloproteinases (TIMPS), growth factors such as transforming growth factor $\beta$, bone morphogenetic proteins, fibroblast growth factor, epithelial growth factor, anti-apoptotic agents, antibiotics, anti-inflammatory drugs, and so forth.

When considering a multi-laminar balloon material, the individual sheets of the balloon material can be modified with varying amounts of biologically active agents. For instance, different amounts of cell attracting agents such as, without limitation, glucose, serum proteins, chemokines, peptides, etc. can be included in different sheets of the balloon material so as to create a gradient that can entice host cells to enter into the balloon (e.g., higher concentration of attractant molecules on the inside balloon layers and lower concentration of attractant molecules in the outer layers of the balloon can draw cells toward the inside of the balloon towards the filler material). This can encourage integration of the nucleus pulposus replacement with the surrounding tissue following implantation.

The containment balloon material can be modified to include other compounds that may serve other purposes as desired. For instance, the containment balloon material can be modified to include radio-opaque agents such that the device could be visualized with traditional medical imaging technology during and/or following implantation of the device.

Referring again to FIG. 1, a closure device 14 is combined with the containment balloon 12 to form the nucleus pulposus replacement 10. The closure device 14 includes a nut 20, an outer ring 24 and an injection port 22, which fit together in conjunction with the containment balloon 12.

Figure 3A:
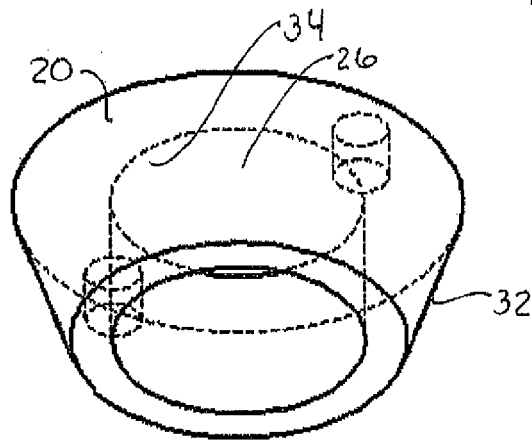
FIG. 3 illustrates a perspective view (FIG. 3A), a side view (FIG. 3B), and a top view (FIG. 3C) of a nut that is a portion of a closure assembly for a nucleus pulposus replacement.
Figure 3B:
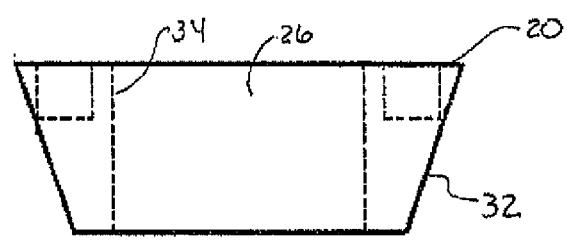
Figure 3C:
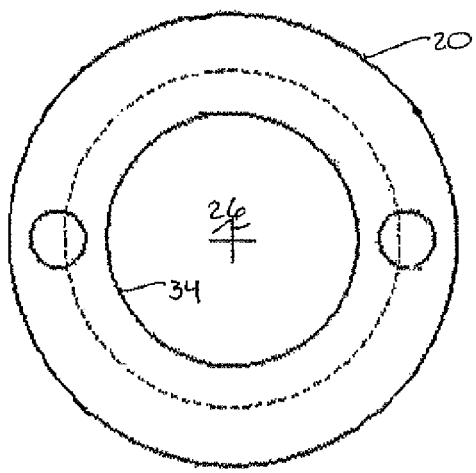
Figure 4A:
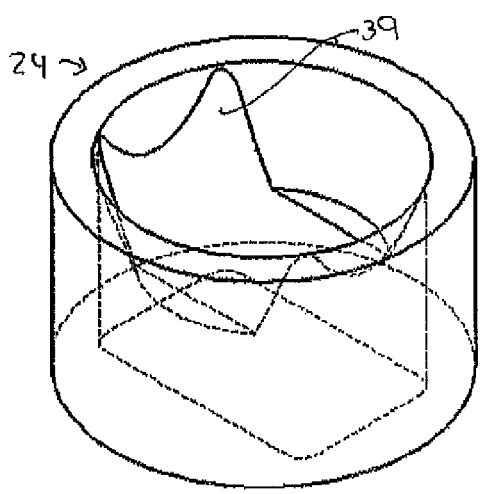
FIG. 4 illustrates a perspective view (FIG. 4A), a top view (FIG. 4B), a first side view (FIG. 4C) and a second side view (FIG. 4D) of an outer ring that is a portion of a closure assembly for a nucleus pulposus replacement.
Figure 4B:
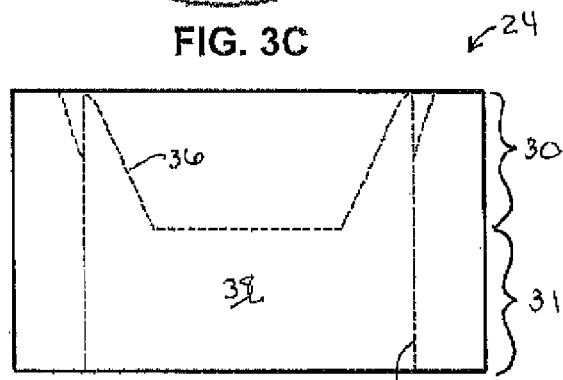
Figure 4C:
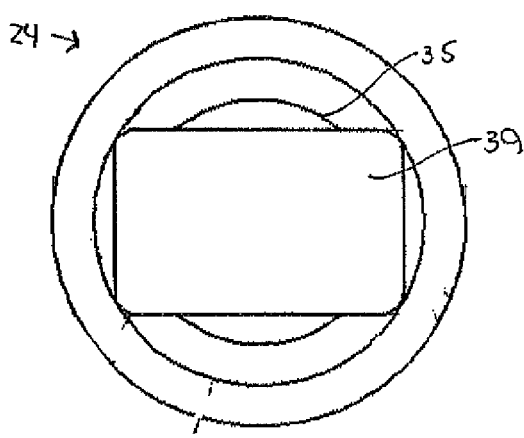
Figure 4D:
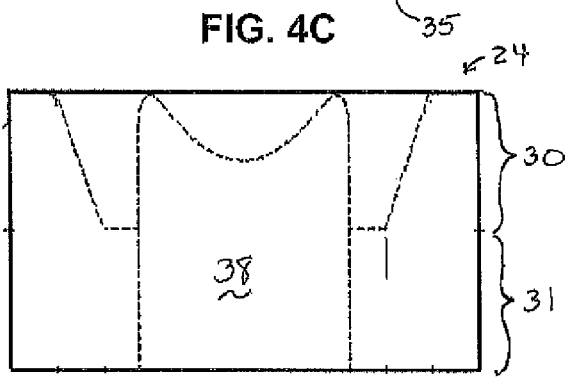
Figure 5A:
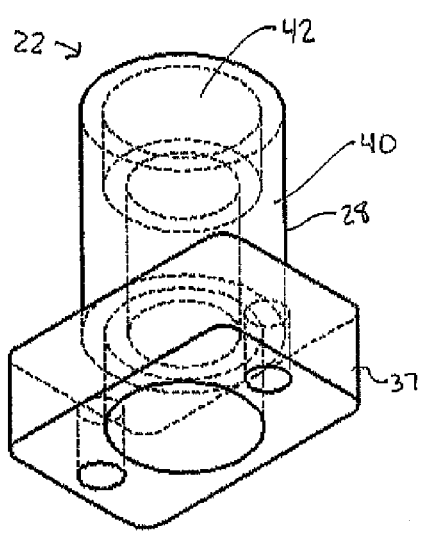
FIG. 5 illustrates a perspective view (FIG. 5A), a top view (FIG. 5B), a first side view (FIG. 5C) and a second side view (FIG. 5D) of an injection port that is a portion of a closure assembly for a nucleus pulposus replacement.
Figure 5C:
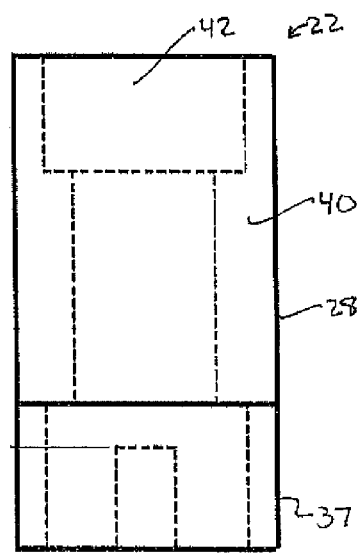
Figure 5B:
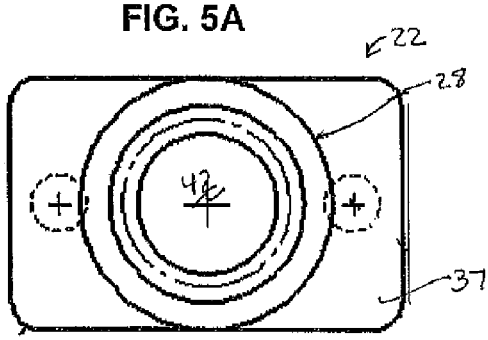
Figure 5D:
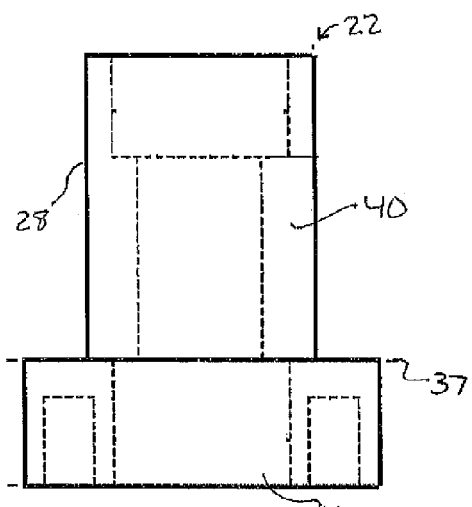

The nut 20 of the closure device 14 is illustrated in more detail in FIG. 3. FIG. 3A is a perspective view of the nut 20, FIG. 3B is a side view of the nut 20 and FIG. 3C is a top view of the nut 20. As can be seen, the nut 20 has a generally circular cross section, a beveled outer surface 32 and an inner surface 34 that defines a cylindrical passage 26 through the nut. The particular shape of the nut is not critical, though the nut is designed to be seated in the upper section 30 of the outer ring 24 shown in FIG. 4.

Several views of the outer ring 24 are provided in FIGS. 4A, 4B, 4C, and 4D. As can be seen in the two side views of the outer ring shown in FIGS. 4C and 4D, the outer ring includes an upper section 30 and a lower section 31. The upper section 30 includes an inner surface 36 that is beveled to match the bevel of the outer surface 32 of the nut 20. In this particular embodiment the beveled inner surface 36 is a surface of a cradle 39 that is formed such that the nut 20 can be seated in the cradle 39. A passage 38 passes through the center of the outer ring 24, as shown.

The third component of the closure device 14 is the injection port 22, views of which are provided in FIGS. 5A, 5B, 5C, and 5D. The injection port 22 includes a post 40 and a base 37. The post 40 has an outer surface 28 as shown. The injection port 22 also defines a passage 42 that passes longitudinally through the entire injection port 22. In this particular embodiment, the passage 42 is generally cylindrical, but with wider segments at either end of the passage 42. The shape of the passage 42 can be designed in one embodiment to dock with a device such as a syringe that can be used to fill the containment balloon with fill material, for instance following implantation.

Referring again to FIG. 1, following assembly of the closure device 14, the post 40 of the injection port 22 can fit within the passages of the nut 20 and the outer ring 24. The containment balloon 12 is attached to the closure device 14 with a first portion 50 of the containment balloon 12 held between the outer beveled surface 32 of the nut 20 and the inner matching beveled surface 36 of the upper section 30 of the outer ring 24, a second portion 52 of the containment balloon 12 held between the outer surface 28 of the post 40 of the injection port 22 and the matching inner surface 35 of the lower portion 31 of the outer ring 24, and a third portion 54 of the containment balloon wrapping the base 37 of the injection port 22.

Also included in the closure device 10 is a one-way port 16 that is within the passage 42 of the injection port 22. The one-way port 16 can be formed of a self-sealing material, generally a soft elastomer, that can be located within all or a portion of the passage 42. For example, the one-way port 16 can be formed of a silicone rubber or some other soft, biocompatible elastomer that can fill and seal the passage 42. The one-way port 16 can be located within the passage 42 either prior to or following assembly of the other components of the nucleus pulposus replacement, as desired. During use, a fill device such as a syringe needle can penetrate the one-way port in order to fill the containment balloon with a suitable fill material and following removal of the fill device, the one-way port can seal so as to prevent leakage of the fill material 18 from the containment balloon 12.

Figure 6:
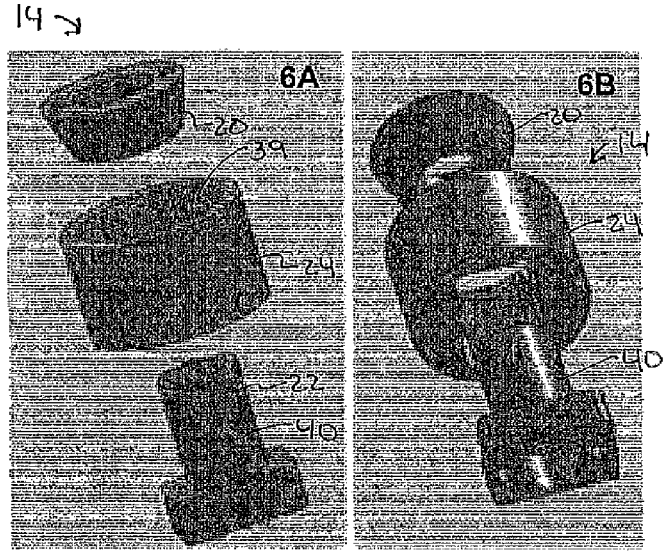
FIG. 6A and FIG. 6B are two perspective views of a closure assembly for a nucleus pulposus replacement.

FIG. 6A and FIG. 6B show two perspective exploded views of the closure device 14 that illustrate the assembly of the components absent the containment balloon. As shown, the nut 20 fits into the cradle 39 of the outer ring 24 and the post 40 of the injection port 22 passes through the passages of both the outer ring 24 and the nut 20.

The overall dimensions of the closure device can be such that the nucleus pulposus replacement can fit into the intervertebral disc area. For instance, the closure device can define a cross-sectional dimension of less than about 15 millimeters (mm), or less than about 10 mm, in one embodiment. For example, the closure device can have overall height and width dimensions of from about 2 millimeters to about 7 millimeters.

As described above, in conjunction with the assembly of the closure device and as illustrated in FIG. 1, a portion 52 of the containment balloon 12 can be wrapped around the base 37 of the injection port 22 and additional portions of the containment balloon can be sandwiched between the post 40 of the injection port 22 and the lower portion 31 of the outer ring 24 and also between the upper portion 30 of the outer ring 24 and the outer edge 34 of the nut 20. Following assembly, the closure device 14 and the containment balloon 12 can be securely held together according to any suitable system. For instance, a component of the closure device 14 can be formed with pins or posts on a surface and the mating surface of the mating component can be formed with notches, grooves, indentations, etc. that can mate with the pins or posts upon assembly. The cross-sectional dimension of the notch or groove can be slightly less than that of the post or pin, so as to form a tight fit between the two, particularly when a portion of the containment balloon is also sandwiched between the two mating surfaces.

Figure 7:
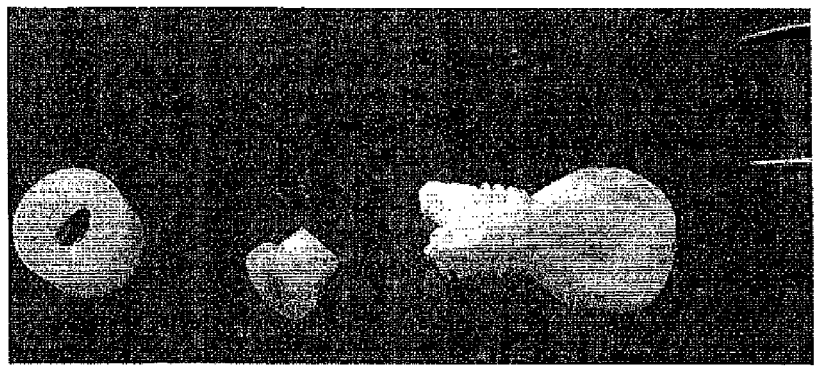
FIG. 7 illustrates another embodiment of a closure assembly.

In another embodiment illustrated in FIG. 7, the mating surfaces of the closure device components can be threaded as shown so as to secure the components to one another. In this embodiment, the threads can be designed so as to allow the location of the containment balloon portions between the mating surfaces and form a secure connection between the various components.

Adhesion between the surfaces can also be obtained through the formation of a bond between the various components, for instance through the application of heat and/or pressure to the closure device following assembly, which can soften a thermoplastic material as may be used to form the closure device and secure the closure device components and the containment balloon material together.

Figure 2:
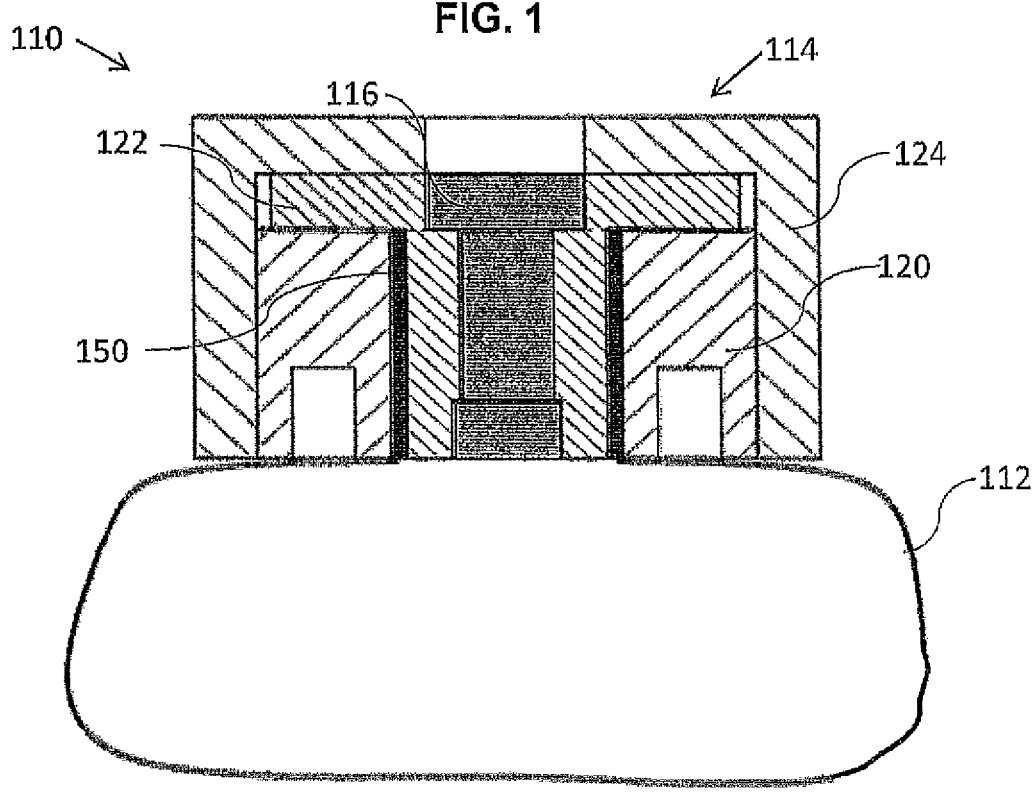
FIG. 2 illustrates another embodiment of a nucleus pulposus replacement including as described herein.

Of course, the specific design of the closure device is not critical, and other closure devices may alternatively be utilized that can provide a one-way port for furnishing the containment balloon with a fill material. By way of example, FIG. 2 illustrates another embodiment of a nucleus pulposus replacement 110 that includes a containment balloon 112, and a closure device 114. The closure device 114 includes a nut 120, an outer ring 124, and an injection port 122. As can be seen, in this embodiment, a portion 150 of the containment balloon 112 is secured between the injection port 122 and the nut 120, for instance between the threads of the threaded components 112, 122. In addition the outer ring 124 is secured over both of the injection port 122 and the nut 120 with access available for a fill device such as a syringe to the one-way port 116. As shown, the closure device 114 is attached to the containment balloon 112 such that a large surface area of the closure device 114 is exposed. Following implant, this surface area 114 can be in contact with surrounding tissue at the implant site. In comparison, the nucleus pulposus replacement 10 illustrated in FIG. 1 includes a closure device 14 that is attached to the containment balloon 12 such that little surface are of the closure device 14 will be exposed to surrounding tissues following implant. Rather, a larger portion of the surface area of the closure device 14 is held in contact with the containment balloon 12.

Materials as may be used to form the closure device can generally include any formable biocompatible, implantable materials including degradable and non-degradable materials, as desired. By way of example, the components of a closure device can be formed of the same or different materials including, without limitation, homopolymers or copolymers of poly(ether ether ketone), thermoplastic polyurethanes, polyamides, polycarbonates, poly(lactic acid), poly (hydroxyalkanoate), and so forth. Formation methods can include injection molding, casting, etc. Materials used in forming the closure device as well as the containment balloon include those that can be sterilized, for instance using standard peracetic acid sterilization procedures.

A closure device can incorporate additional materials that may provide a desirable function. For instance, a closure device can be formed to include a radio-opaque marker incorporated in or on the device that can improve visualization of the nucleus pulposus replacement with traditional medical imaging technology. Such a modification can ease implantation and filling of the device as well as post-operative visualization to determine, e.g., the level of degradation of the device and the incorporation of native cells and tissue into the device, in the case of degradable materials.

The outer surface of the closure device that can contact the surrounding tissue at the implant site can be treated to better adhere at the site. For example the exposed surface can include structural features such as hooks, barbs, eyelets, and so forth that can provide attach to surrounding tissue and help to anchor the nucleus pulposus replacement at the implant site.

Additionally or alternatively, the outer surface of the closure device that can contact surrounding tissue at the implant site can be coated with an adhesive, for instance a tissue adhesive that can help to anchor the replacement. Other materials may be coated on the surface of the closure device such as growth factors, anti-inflammatory agents, antibiotics, etc. that can be released following implant. For example, a gel, e.g., an implantable hydrogel formed of e.g., collagen, chitosan, alginate, hyaluronan, dextran, etc. can form a coating on the closure device, and the hydrogel can be loaded with one or more biologically active agents that can be released from the coating following implant.

Figure 8:
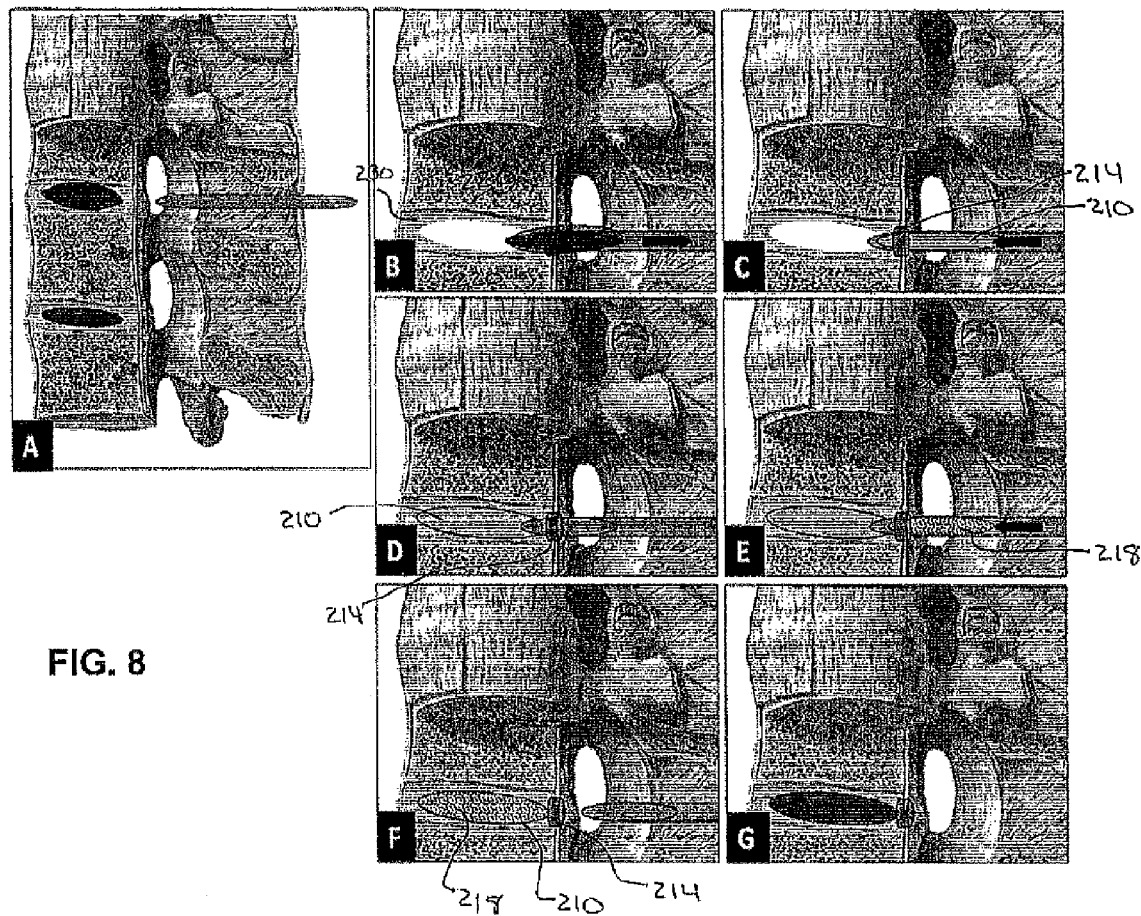
FIG. 8A-FIG. 8G illustrate a method for inserting a nucleus pulposus replacement into the intervertebral disc space and filling the replacement with a fill material.

FIG. 8 illustrates one method of utilizing the nucleus pulposus replacement. Initially, access is obtained to the IVD area via standard surgical devices, as shown at FIG. 8A. Beneficially, due to the small size or the nucleus pulposus replacement prior to furnishing a fill material to the interior of the containment balloon, minimally invasive surgical methods can be utilized for insertion. At FIG. 8B, damaged nucleus pulposus tissue is removed from the IVD area leaving surrounding annulus fibrosis 230 and cartilaginous endplates 220. A nucleus pulposus replacement 210 is then inserted into the formed void (FIG. 8C) with the closure device 214 accessible at the insertion point (FIG. 8D).

Following insertion the nucleus pulposus replacement can be utilized as-is, i.e., without the addition of any fill material located in the interior of the containment balloon. For instance, the nucleus pulposus replacement can be used as a tissue plug or patch to reinforce defects in the annulus fibrosus. Alternatively, a fill material 218 can be located within the nucleus pulposus replacement 210 via the one-way port of the closure device 214, as illustrated at FIG. 8E such that the nucleus replacement device can fill a larger void. The fill material can provide support to the device and replace the damaged nucleus pulposus tissue that has been previously removed.

In general, a fill material can be a liquid or a viscous fluid that can form a gel matrix or a viscous fluid matrix. As utilized herein, the term "gel matrix" generally refers to a colloid in which a dispersed phase (e.g., a crosslinked polymer) is in combination with a continuous phase (e.g., water) to produce a viscous semisolid jelly-like product. In one embodiment, the fill material can be a hydrogel. Hydrogels are water-swollen and cross-linked gel matrix polymeric structures, usually having low modulus and compressive strength. Due to their soft and flexible structure, hydrogels may be used as a space-filling material as well as a cell-delivery device.

The gel matrix may be delivered in a final form, i.e., following all polymerization and cross-linking. Alternatively, gelling can partially occur prior to delivery to a containment balloon, and can then completely gel after delivery, or gelling may occur entirely following delivery. For example, as illustrated in FIG. 8F, and fill material 218 can be delivered to the nucleus pulposus replacement 210 via the closure device 214 and then, following delivery, final cross-linking of the fill material can be carried out, as illustrated at FIG. 8G. There are different methods of crosslinking or otherwise binding a dispersed phase of a gel. For example, a chemical crosslinking agent may be used or crosslinking may occur upon shift in pH or temperature.

Combinations of materials can also be utilized as a fill material for a containment balloon. By way of example, a combination of alginate and gelatin can be used as a fill material.

A fill material may include one or more compounds, each of which can be biodegradable or non-biodegradable, absorbable or non-absorbable, and so forth. A carrier may be made from naturally derived materials, synthetic materials, or a combination thereof. A fill material may also be cellular or acellular. For instance, cells or cellular extracts can be incorporated into a fill material during the preparation of the fill material. By way of example, the fill material and/or the containment balloon can be seeded with autologous cells obtained from biopsies such as adipose-derived mesenchymal stem cells obtained from fat tissue biopsies.

Examples of fill materials can include, but are not limited to, agarose, alginate, collagen, carrageenan (a carboxylated seaweed polysaccharide), chitosan and derivatives thereof. Examples of suitable biodegradable or absorbable biocompatible compounds as may be included in a fill material can include, but are not limited to, derivatives of polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, dextran, dextrin, starch, cellulose, chitosan, demineralized bone matrix and the like and copolymers of the same. Additional examples of fill material can include decellularized human or animal nucleus pulposus material, elastin-chondroitin sulfate-hyaluronic acid-collagen composite materials, chitosan-based materials, and gellam gum-based materials.

According to one embodiment, a fill material can be a non-biodegradable material formed by hydrating the triblock polymer poly(ethylene oxide)-polypropylene oxide)poly (ethylene oxide), which is commercially available under the PLURONIC™ or POLOXAMER™ trade names. Other carrier materials can include those that include synthesized macromers having a poly(ethylene glycol) central block, extended with oligomers of α-hydroxy acids such as oligo(d,l-lactic acid) or oligo(glycolic acid) and terminated with acrylate groups. Such macromers can be rapidly polymerized with visible light in the presence of a non-toxic photoinitiator to form crosslinked gels. Gels can degrade within a physiological-like environment upon hydrolysis of the oligo(α-hydroxy acid) regions into poly(ethylene glycol), α-hydroxy acid, and oligo(acrylic acid). The degradation rates can be tailored by appropriate choice of the oligo(α-hydroxy acid). Another synthesized biodegradable block copolymeric material as can be utilized as a fill material can be synthesized by transesterification of poly(lactic acid) (PLA) or poly(lactic acid)/glycolic acid (PLA/GA) and poly(ethylene glycol) (PEG). Fill materials are not limited to these specifically disclosed materials, however.

Beneficially, the nucleus pulposus replacement includes a flexible containment balloon and as such can replace and completely fill any void remaining in an intervertebral disc following fill of the balloon with the desired fill material. Moreover, the fill material as well as the balloon can be formed so as to be biodegradable and encourage growth of new, healthy tissue in the void, which can lead to regeneration of the removed and damaged tissue.

The present disclosure may be better understood with reference to the Examples, presented below.

EXAMPLE 1

Acellular elastin-collagen sheets were prepared from porcine pericardium via decellularization to reduce antigenicity and enhance porosity. Fresh adult swine pericardial sacs were cleaned, rinsed in sterile saline, and decellularized as follows. In the first step, tissues were stored in double-distilled water overnight at 48° C. to induce hypotonic shock and cell lysis. After rinsing, tissues were treated with 0.25% sodium-deoxycholate, 0.15% Triton X-100, 0.1% ethylenediaminetetraacetic acid (EDTA), 0.02% sodium azide ($NaN_3$), in 50 mM Tris-hydrochloric acid (HCl) buffer (pH 7.8) with mild agitation for 6 days at 228° C. and changes of the solution after 3 days.

After rinsing with double-distilled water and 70% ethanol to remove detergents, tissues were treated with a deoxyribonuclease/ribonuclease mixture (360 mU/mL for each enzyme) at 378° C. for 24 h to fully digest away nucleic acids. This was followed by rinsing twice with double-distilled water. Finally acellular sheets were rinsed with 70% ethanol, sterile saline and stored in sterile saline with 0.02% $NaN_3$ at 4° C.

Figure 9:
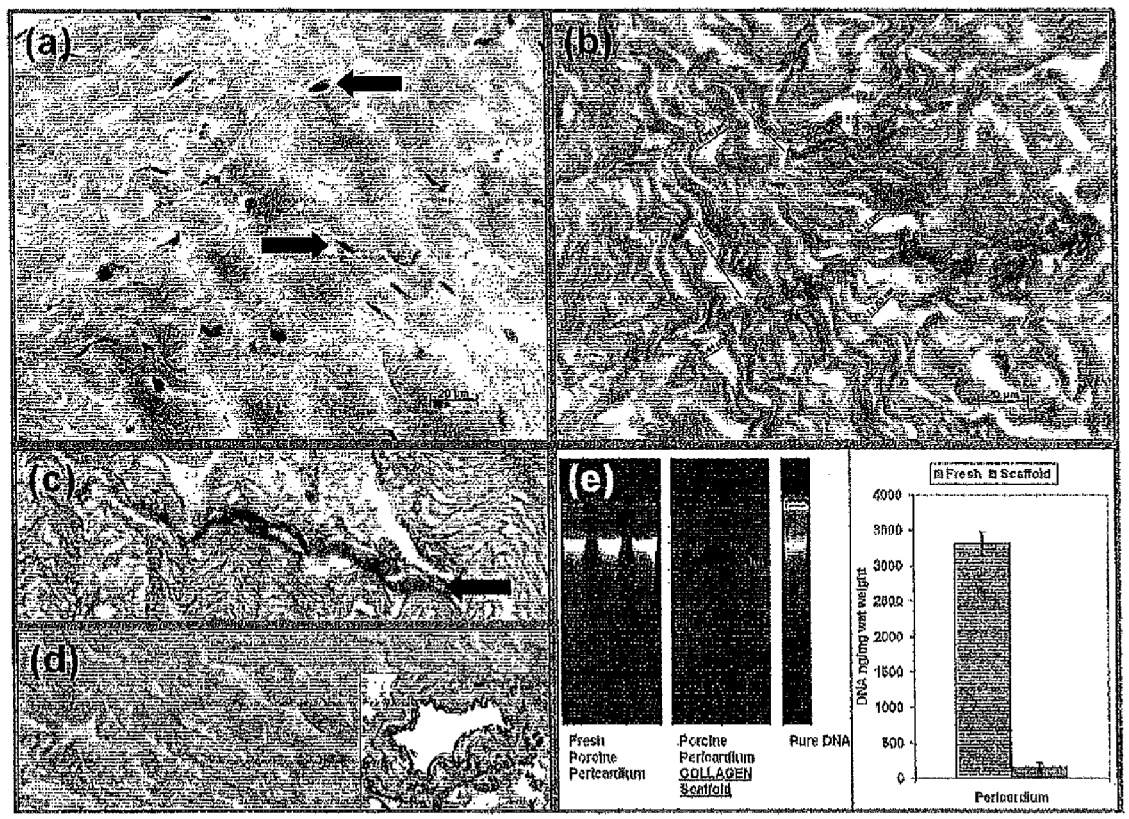
FIG. 9A illustrates fresh porcine pericardium.
FIG. 9B illustrates a sheet formed of decellularized porcine pericardium.
FIG. 9C illustrates the results of histochemistry using biotinylated *Griffonia simiplicifolia* lectin to detect the presence of the xenoantigen Galα-1-3Gal (Galα), the main epitope responsible for rejection of organ transplants, in fresh porcine pericardium.
FIG. 9D illustrates the results of histochemistry using biotinylated *G. simiplicifolia* lectin to detect the presence of Galα in a sheet formed of decellularized porcine pericardium.
FIG. 9E illustrates the results of DNA analysis of fresh porcine pericardium and a sheet formed of decellularized porcine pericardium.

Gravimetry revealed 81+/−0.8% water content, which was significantly higher (p<0.05) than fresh pericardium (77.2+/−0.7%). Hematoxylin and Eosin (H&E) histological staining of the fresh pericardium is shown in FIG. 9A and the treated acellular sheets are shown in FIG. 9B. The arrows of FIG. 9A point to cells. As can be seen, complete cell removal was obtained by the procedure. Pore sizes evaluated from histology ranged between 8 and 35 microns.

To detect the presence of the xenoantigen Galα-1-3Gal (Galα), the main epitope responsible for rejection of organ transplants, histochemistry was performed using biotinylated *Griffonia simplicifolia* lectin. Results showed positive Galα reaction in fresh porcine pericardium (mostly around capillaries) (FIG. 9C, arrow) but none in fibroblasts or the collagen matrix and virtually undetectable presence of the antigen in the decellularized collagenous sheets (FIG. 9D) indicating that decellularization completely removed Galα antigen from porcine pericardium, thus reducing potential biocompatibility issues in human applications.

To further confirm decellularization, genomic DNA was extracted and purified from the decellularized sheets and from native tissues as controls, and DNA samples subjected to agarose gel electrophoresis followed by densitometry (FIG. 9E). DNA analysis confirmed complete cell removal of DNA (reduction of DNA content by >95%).

Figure 10:
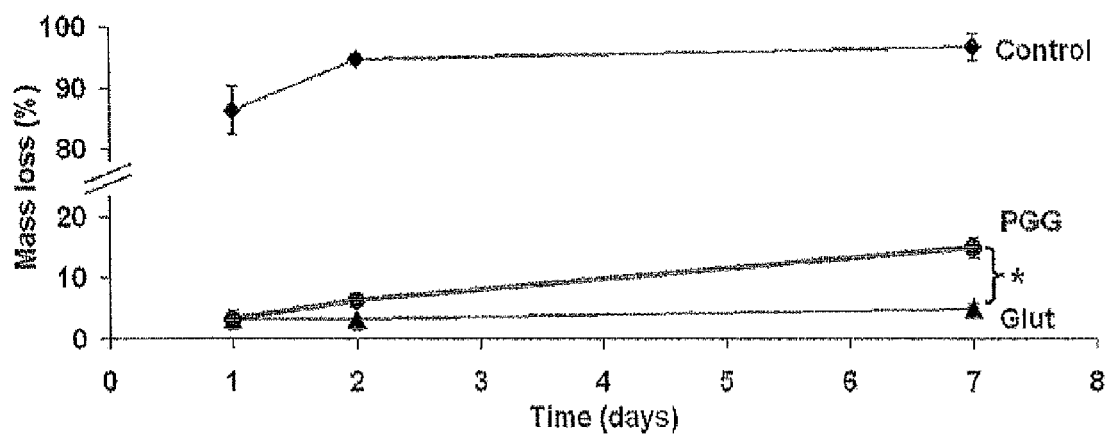
FIG. 10 graphically illustrates the degradation of a decellularized sheet over time by collagenase for a control (no stabilization), a sheet stabilized with glutaraldehyde, and a sheet stabilized with pent-galloyl glucose (PGG).

The acellular collagen sheets were incubated with pentagalloyl glucose (PGG, 0.3% in 50 mM Hepes buffered saline pH 5.5 for 48 hours at 22° C.) and rinsed. The biodegradability of PGG-treated collagen sheets was tested by exposure to collagenase using untreated sheets and glutaraldehyde fixed sheets (Glut) as controls. Collagen sheets (n=3 per group) were lyophilized, weighed and incubated with 6.25 Units/ml collagenase at 37° C. and mass loss evaluated after 1, 2 and 7 days by measuring dry weight before and after collagenase (FIG. 10). Results showed progressive mass decrease in controls indicating that the fibrous collagen is fully biodegradable. PGG-treated fibrous collagen sheets lost minimal mass (2 and 4%) during same time frame, but started to slowly degrade (14% mass loss after 7 days, 23% after 20 days) strongly suggesting that PGG is an efficient fixation agent for collagen and that PGG could control collagen degradation. Studies also showed that PGG is capable of stabilizing elastin and GAGs (data not shown).

Figure 11A:
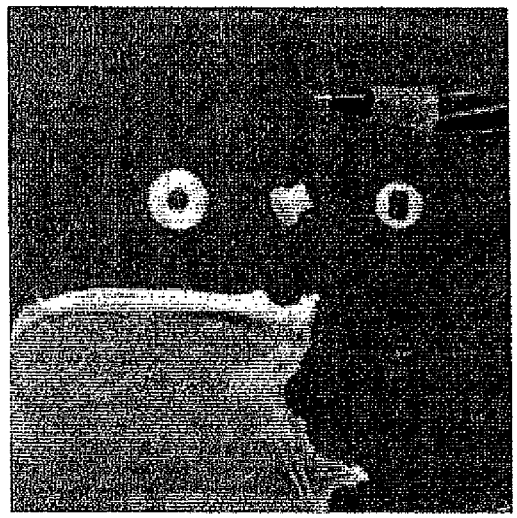
FIG. 11A illustrates the components of a nucleus pulposus replacement.
Figure 11B:
FIG. 11B illustrates the components of FIG. 10A following assembly.
Figure 11C:
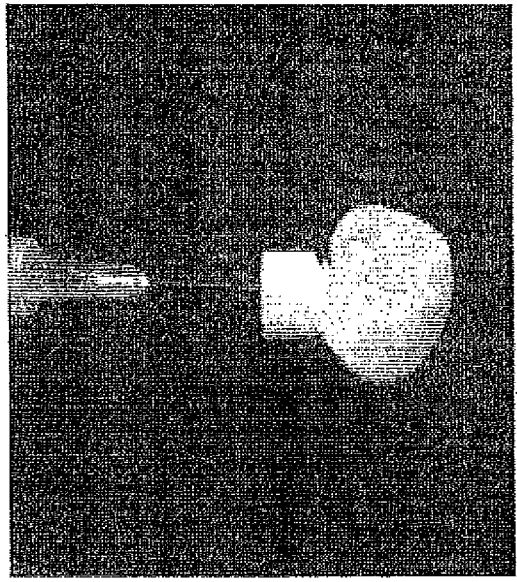
FIG. 11C illustrates the assembled nucleus pulposus replacement of FIG. 10B during filling of the balloon of the replacement.

Mechanical properties of the acellular collagen sheets were characterized with a biaxial test system and via burst strength testing. Two burst testing regimes were performed; 1) a multi-axial burst test using a Mullen's textile testing apparatus to assess the strength of the individual acellular pericardial sheets and, 2) burst testing using a custom-designed test rig to assess the burst strength of the containment balloon assembly as illustrated in FIG. 11A (separated components), FIG. 11B (following assembly), and FIG. 11C (during fill).

For the multi-axial burst testing of acellular pericardial sheets, specimens (n=6) were secured in the apparatus by clamping between two steel rings. A diaphragm located below the lower steel ring was then inflated by fluid pressure until the specimen ruptured. The burst strength was determined as the difference between the total pressure required to burst the specimen and the pressure required to inflate the diaphragm. Containment balloon (n=3) burst testing was performed on an MTS 4500 electro-mechanical test frame fitted with a 10 kN load cell. Testing was carried out at a speed of 25 mm/minute using containment balloons filled with water. All results were represented as a mean±standard error.

Figure 12:
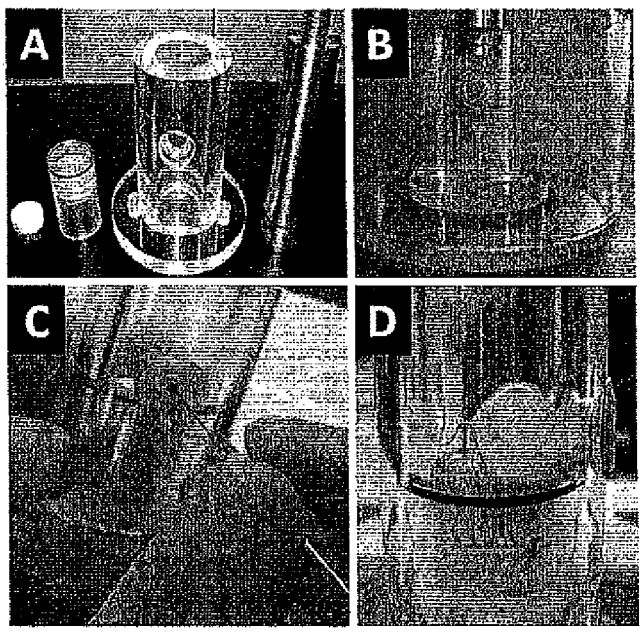
FIGS. 12A-12D illustrate a testing rig that was designed to test the overall compressive strength of a nucleus pulposus replacement.

A testing rig was designed to test the overall compressive strength of containment balloon system as a whole (FIG. 12). Components of the testing rig included a stainless steel support stand, a polished acrylic confining chamber with threaded one-way valve adapter and locating pins and a porous fluid collection container including a one-way valve adapter plug (FIG. 12A), and a cylindrical porous (15-40 μm) polyethylene insert stainless steel compression platen with a dynamic o-ring seal (FIG. 12B). The polished surfaces of the testing rig allowed for image capture and specimen analysis from all sides during testing, including from underneath. At FIG. 12C the containment balloon of FIG. 11 is inflated and compression testing was carried out as shown at FIG. 12D without interference of the one-way valve.

Average burst strength of a single acellular pericardial sheet using the Mullen's apparatus was 0.37±0.04 MPa. When two acellular pericardial sheets were layered and the orientation of collagen fibers within the sheets was offset by 90°, the burst strength increased to approximately 0.90 MPa. When containment balloon samples were assembled with the first generation closure, inserted into the testing rig and inflated with water, the maximum compressive stress achieved before failure was 1.34±0.04 MPa. The failure mode noted was damage of the balloon material at the balloon-valve interface. It was noted during testing that some fluid was able to escape thru the pores of the balloon and enter into the porous collection container. No water seepage from the silicone injection port was observed.

Results from these tests indicated the suitability of this material for the described application. Additionally, acellular collagenous sheets were shown to possess excellent in vivo biocompatibility and no calcification when implanted subdermally in juvenile rats. Notably PGG-fixed collagen sheets showed moderate cell infiltration, mainly by cells positive for vimentin and 4-Prolyl hydroxylase (fibroblast markers) and smooth muscle cell actin (myofibroblast marker) in the absence of detectable macrophages, cytotoxic T-lymphocytes and lgG deposits indicating that the scaffolds did not elicit immune or inflammatory reactions in the subject. Phenol staining showed that PGG binds to the collagen fibers and PGG was still collagen-bound after implantation for 21 days and 40 days.

EXAMPLE 3

Figure 13:
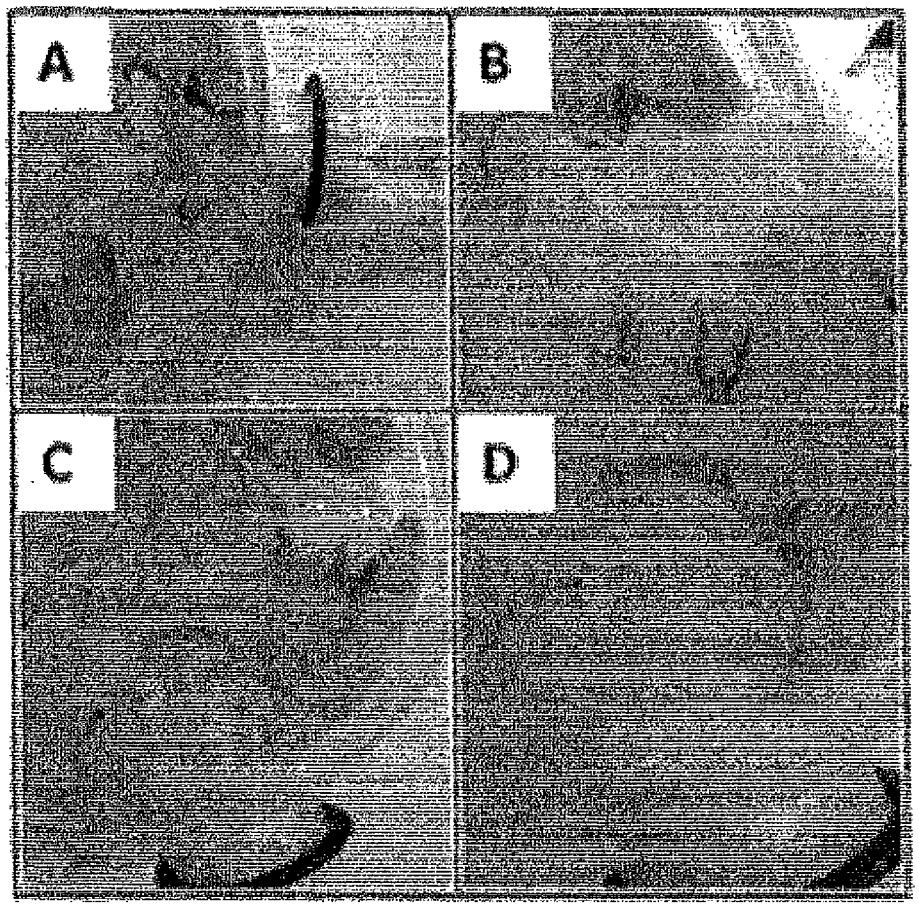
FIG. 13A illustrates irregular shaped voids formed in a synthetic degenerated intervertebral disc, one of which is being filled with a nucleus pulposus replacement as described herein.
FIG. 13B illustrates the nucleus pulposus replacement of FIG. 11A at increased magnification.
FIG. 13C illustrates a second nucleus pulposus replacement filling a second void of the synthetic degenerated intervertebral disc of FIG. 11A.
FIG. 13D illustrates the second nucleus pulposus replacement of FIG. 11C at increased magnification.

To illustrate and assess the ability of the containment balloons to be implanted and inflated to completely fill irregular shaped voids, a silicone-based model was manufactured. The model (FIG. 13A) consisted of a cylindrical silicon rubber insert into which an irregular shaped void was carved representing a void space left in the NP region of the intervertebral disc space following nucleotomy. Inserts were secured between two polystyrene culture dishes to allow for visual assessment for void space filling. Containment balloons were inserted into the models and were inflated through the one-way valve with water filled syringes. Digital images were captured (FIGS. 13A-13D) in order to qualitatively assess the fit of the device within the void.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A nucleus pulposus replacement comprising:
   a containment balloon, the containment balloon comprising multiple layered sheets, each of which including elastin and collagen; and
   a closure device, the closure device being joined to the containment balloon, the closure device including a one-way port for furnishing a fill material to an interior of the containment balloon.

2. The nucleus pulposus replacement of claim 1, wherein the multiple layered sheets comprise fibrous plies, the plies of adjacent sheets being at an angle to one another.

3. The nucleus pulposus replacement of claim 1, wherein the sheets are formed of a source tissue that has been decellularized.

4. The nucleus pulposus replacement of claim 1, wherein the containment balloon is porous.

5. The nucleus pulposus replacement of claim 1, wherein at least one of the elastin and the collagen are cross-linked.

6. The nucleus pulposus replacement of claim 5, wherein the elastin is cross-linked with pentagalloyl glucose.

7. The nucleus pulposus replacement of claim 1, wherein the containment balloon exhibits a compressive stress before failure of greater than about 1 MPa.

8. The nucleus pulposus replacement of claim 1, wherein the sheets of the containment balloon have been loaded with one or more biologically active agents.

9. The nucleus pulposus replacement of claim 1, wherein the closure device comprises multiple components.

10. The nucleus pulposus replacement of claim 9, wherein a portion of the containment balloon is sandwiched between components of the closure device to join the containment balloon to the closure device.

11. The nucleus pulposus replacement of claim 1, wherein at least one of the containment balloon and the closure device is degradable.

12. The nucleus pulposus device of claim 11, wherein both the containment balloon and the closure device are degradable.

13. A method for forming the nucleus pulposus device of claim 1, the method including joining the containment balloon to the closure device.

14. The method according to claim 13, wherein the closure device comprises multiple components, the method comprising locating a portion of the containment balloon between components of the closure device.

15. The method according to claim 13, the method further comprising modifying an outer surface of the containment balloon.

16. The method according to claim 13, further comprising modifying an outer surface of the closure device.

17. A method for replacing nucleus pulposus tissue, the method comprising:
   removing nucleus pulposus tissue from an intervertebral disc to form a void in the intervertebral disc; and
   inserting a nucleus pulposus replacement into the void, the nucleus pulposus replacement comprising
      a containment balloon, the containment balloon comprising a sheet that includes elastin and collagen, and
      a closure device, the closure device being joined to the containment balloon, the closure device including a one-way port for furnishing a fill material to an interior of the containment balloon.

18. The method of claim 17, the method further comprising furnishing the fill material to the interior of the containment balloon via the one-way port.

19. The method of claim 18, wherein the fill material is a gel matrix.

20. The method of claim 19, wherein the gel matrix is furnished to the interior of the containment balloon in final form.

21. The method of claim 19, wherein the gel matrix is finally cross-linked following furnishing of the fill material to the interior of the containment balloon.

22. A nucleus pulposus replacement comprising:
   a containment balloon, the containment balloon comprising a sheet that includes elastin and collagen, the elastin being crosslinked with pentagalloyl glucose; and
   a closure device, the closure device being joined to the containment balloon, the closure device including a one-way port for furnishing a fill material to an interior of the containment balloon.

23. The nucleus pulposus replacement of claim 22, wherein the containment balloon comprises multiple layered sheets.

24. The nucleus pulposus replacement of claim 23, wherein the multiple layered sheets comprise fibrous plies, the plies of adjacent sheets being at an angle to one another.

25. The nucleus pulposus replacement of claim 22, wherein the sheet is formed of a source tissue that has been decellularized.

26. The nucleus pulposus replacement of claim 22, wherein the sheet of the containment balloon has been loaded with one or more biologically active agents.

27. A nucleus pulposus replacement comprising:
a containment balloon, the containment balloon comprising a sheet that includes elastin and collagen, wherein the containment balloon exhibits a compressive stress before failure of greater than about 1 MPa; and
a closure device, the closure device being joined to the containment balloon, the closure device including a one-way port for furnishing a fill material to an interior of the containment balloon.

28. The nucleus pulposus replacement of claim 27, wherein the containment balloon comprises multiple layered sheets, each of which including elastin and collagen.

29. The nucleus pulposus replacement of claim 28, wherein the multiple layered sheets comprise fibrous plies, the plies of adjacent sheets being at an angle to one another.

30. The nucleus pulposus replacement of claim 27, wherein the sheet is formed of a source tissue that has been decellularized.

31. The nucleus pulposus replacement of claim 27, wherein the sheet of the containment balloon has been loaded with one or more biologically active agents.

32. The nucleus pulposus replacement of claim 27, wherein at least one of the elastin and the collagen are cross-linked.

\* \* \* \* \*